United States Patent
Kloster

(10) Patent No.: US 8,695,143 B2
(45) Date of Patent: Apr. 15, 2014

(54) MECHANICAL DRIVE TRAIN WITH A MOTOR AND AN ECCENTRIC FOR A RESONANT POWER TOOTHBRUSH

(75) Inventor: Tyler G. Kloster, Snoqualmie, WA (US)

(73) Assignee: Koninklijke Philips N.V., Eindhoven (NL)

( * ) Notice: Subject to any disclaimer, the term of this patent is extended or adjusted under 35 U.S.C. 154(b) by 35 days.

(21) Appl. No.: 13/513,614

(22) PCT Filed: Nov. 22, 2010

(86) PCT No.: PCT/IB2010/055344
§ 371 (c)(1),
(2), (4) Date: Jun. 4, 2012

(87) PCT Pub. No.: WO2011/077287
PCT Pub. Date: Jun. 30, 2011

(65) Prior Publication Data
US 2012/0246845 A1    Oct. 4, 2012

Related U.S. Application Data

(60) Provisional application No. 61/289,489, filed on Dec. 23, 2009.

(51) Int. Cl.
*A61C 17/22*    (2006.01)

(52) U.S. Cl.
USPC ............................................. 15/22.1; 15/22.2

(58) Field of Classification Search
CPC ............... A61C 17/22; A61C 17/3418; A61C 17/3481; A61C 17/34; A46B 13/02
USPC ............ 15/22.1, 22.2, 22.3, 22.4, 23; 310/50, 310/51, 80, 81
See application file for complete search history.

(56) References Cited

U.S. PATENT DOCUMENTS

| 3,183,538 | A | 5/1965 | Hubner |
| 4,149,291 | A | 4/1979 | Stoltz |
| 7,067,945 | B2 * | 6/2006 | Grez et al. ...................... 310/50 |
| 8,418,300 | B2 * | 4/2013 | Miller et al. ................... 15/22.1 |
| 2003/0204924 | A1 | 11/2003 | Grez et al. |
| 2008/0028547 | A1 | 2/2008 | Miller et al. |
| 2009/0070947 | A1 | 3/2009 | Baertschi et al. |

FOREIGN PATENT DOCUMENTS

| DE | 4222455 A1 | 1/1994 |
| GB | 2425050 A | 10/2006 |
| WO | 02054906 A1 | 7/2002 |

* cited by examiner

*Primary Examiner* — Shay Karls

(57) ABSTRACT

The toothbrush includes a drive assembly comprising a DC motor (12) driven by a battery (15) with a rotating drive shaft (16) extending from one end of the DC motor, on which is mounted an eccentric member (20) which rotates with the drive shaft. A spring assembly (24) includes a hub member (26) at a proximal end, a mount member (28) at a distal end and a V-spring member (41) mounted to and extending therebetween. The DC motor is fixed to a rear surface of the hub member, the motor and the hub member being free to move in unison in operation of the toothbrush. The mount member is fixed in position in the toothbrush. A brushhead shaft (38) is mounted to and extends between the hub member and the mount member and extends distally from the mount member. The brushhead shaft member is offset laterally from the axis of rotation of the motor drive shaft. A brushhead assembly (42), including a set of bristles (44), is removably mounted on the brushhead shaft.

10 Claims, 2 Drawing Sheets

MECHANICAL DRIVE TRAIN WITH A MOTOR AND AN ECCENTRIC FOR A RESONANT POWER TOOTHBRUSH

This invention relates generally to resonant-driven power toothbrushes, and more specifically concerns a drive train which includes a DC motor for such a power toothbrush.

Some power toothbrushes use a sinusoidal driven spring assembly to produce an oscillating brushhead action which results in effective cleaning of a user's teeth. However, such a drive train requires custom stators, operating in response to the sinusoidal signal, to create an oscillating magnetic field which drives the spring assembly. Relatively expensive electronic circuits are also necessary in such a system.

The use of a DC motor to drive a resonant power toothbrush is a less expensive alternative. A DC motor drive train is advantageous because of its simplicity in addition to lower cost. A typical DC motor produces a circular action; in an alternative line of development of DC motor-driven power toothbrushes, a spring assembly arrangement is used to provide an oscillating action instead of a circular action. The oscillating action, at selected ranges of frequencies and amplitudes, is known to produce effective cleaning.

In one specific implementation, a DC motor with an eccentric is used to mechanically excite a spring system in a torsion mode, producing the desired resonant oscillating action. However, these particular systems are driven through a flex coupling which oscillates with the spring member. The flex coupling can experience reliability problems. Additionally, in these systems, the eccentric is mounted to rotate in a bushing, which results in wear at the eccentric/bushing interface and is a source of undesirable noise.

It is thus desirable to have a reliable, simple system using a DC motor for mechanically exciting a spring assembly in its resonant mode, with a minimum of parts, while avoiding problems generally associated with magnetic coupling, such as insufficient startup torque and overshoot, which occur when the brush is stalled, causing the motor to run at a higher rpm than desired.

Accordingly, the power toothbrush comprises a driving assembly including a battery and a DC motor, the DC motor having a rotating drive shaft extending from one end thereof; an eccentric member mounted on or connected by another element to the drive shaft and rotatable therewith; a spring assembly which includes a spring member characterized by a stiffness in torsion which results in a rotational system resonant frequency that is lower than the rotational system resonant frequency from bending stiffness, wherein the motor is mounted to a proximal end of the spring assembly, which is free to move, wherein the other end of the spring assembly is fixed in position; a brushhead shaft which is mounted to the spring assembly and extends distally therefrom; and a brushhead, with bristles, attached to the brushhead shaft, wherein in operation the rotation of the eccentric at a selected frequency excites the spring member to an oscillatory action, resulting in the brush shaft and the brushhead oscillating therewith.

Figure 1:
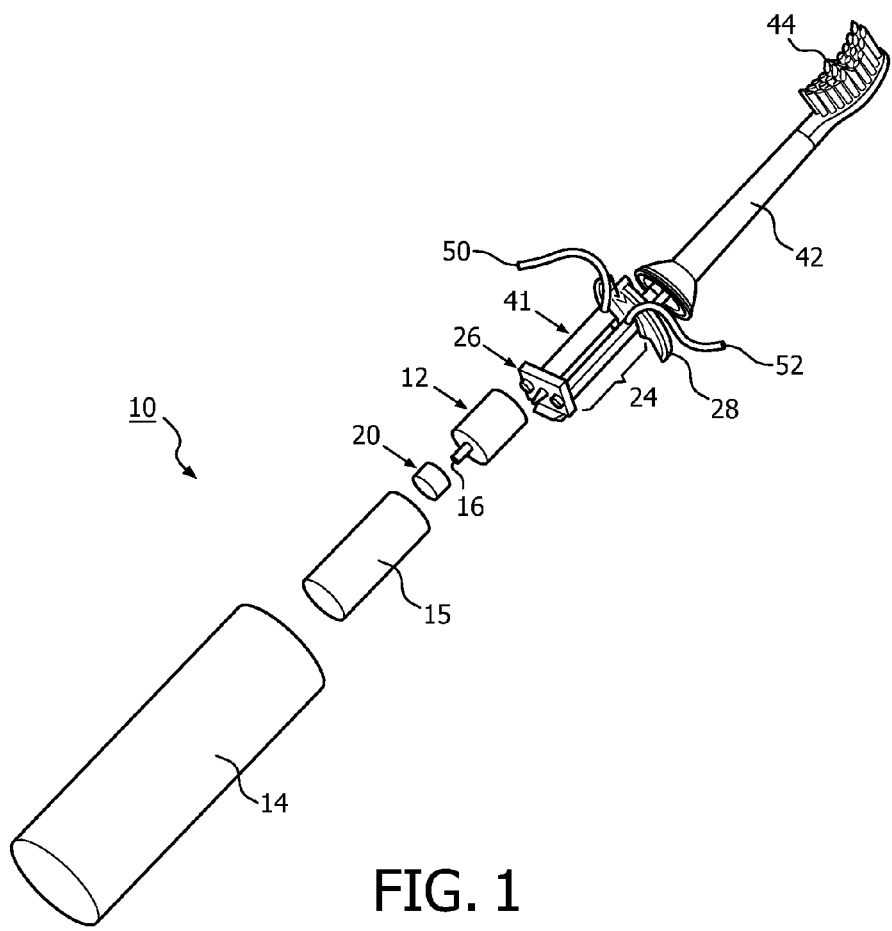
FIG. 1 is an exploded view of the complete toothbrush incorporating the drive train disclosed herein.
Figure 2:
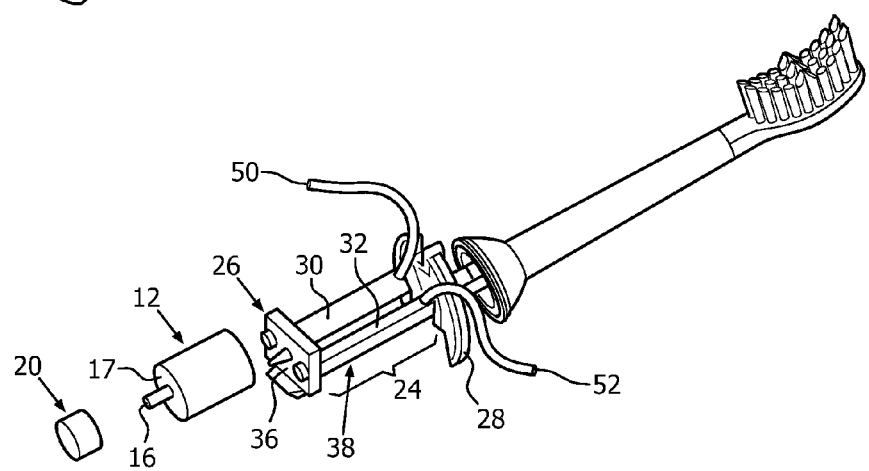
FIG. 2 is an exploded view of a portion of the toothbrush of FIG. 1.

In general, the invention disclosed herein is a DC motor implemented drive train assembly for a resonant power toothbrush for driving a brushhead assembly with an oscillatory action about the axis of the brushhead assembly. The disclosed drive train assembly generates a mechanical force sufficient to excite a spring assembly in a desired resonant mode, which in turn produces the desired oscillatory action of the brushhead assembly portion of the toothbrush. In general, the frequency of the oscillations will be within the range of 100-300 Hz, while the amplitude of the oscillations is within the range of 6°-14°.

Referring now to the figures, a toothbrush 10 includes a DC motor 12, powered by a battery 15. In the embodiment shown, the DC motor is high speed (10K-20K rpm or approximately 160-320 revolutions per second), and low torque, within the range of 0.2 mNm to 1 mNm, although this can be varied.

Motor 12 includes a spinning output shaft 16 which extends out the rear 17 of the motor, in the direction of the rear end of handle 15. Secured fixedly to output shaft 16 is an eccentric 20, which in the embodiment shown is in the form of a disc, although other forms can be used. The eccentric 20 is defined by its mass and its eccentricity, which is the distance from the center of mass of the eccentric to the axis of rotation of the motor output shaft 16. The mass of the eccentric in the embodiment shown is within the range of 0.5-5 grams, while the range of eccentricity is 0.02-5 millimeters.

DC motor 12 is attached to the free end of a spring assembly, shown generally at 24. Spring assembly 24 includes a rear spring hub member 26, a forward spring mount member 28 and two leaf springs 30 and 32 connected between the spring hub member and spring mount member, thus forming a "V" spring member 41. The spring hub member 26 is free to move in operation of the toothbrush, while spring mount member 28 is fixed in position to ground, such as a frame or handle of the toothbrush. The spring hub member 26 and spring mount member 28 are plastic, but could be die cast metal as well. The spring hub member has a symmetrical but irregular shape, as shown most clearly in FIG. 3, although the precise shape is not critical. The spring hub member connects the DC motor to the proximal end of V-spring 41. The spring hub member is approximately 15 mm wide at its widest spot, approximately 15 mm tall and 8 mm thick. As indicated above, DC motor 12 is fixed to the rear surface 36 of the spring hub member and thus moves therewith. The mass movement of inertia of the oscillating mass, which includes DC motor 12, the eccentric 20 and the spring hub member 26, is between 250 and 500 gmm$^2$.

The forward spring mount member as shown is circular in configuration, approximately 25 mm in diameter, with a cut-out portion 39 in the lower portion thereof. The spring mount member is approximately 3 mm thick in the embodiment shown. Again, the particular shape of the forward spring mount is not critical. It is important that the forward spring mount provide a rigid connection to either the handle or an internal frame member.

The two leaf springs 30 and 32 which comprise the V-spring member 41 are identical spring steel, approximately 10-30 mm long, 2-15 mm wide, preferably approximately 5 mm, and a thickness of 0.2 mm to 1.0 mm, preferably approximately 0.5 mm. In the embodiment shown, the angle between the two leaf springs 30 and 32 is in the range of 45°-100°, preferably approximately 70°. The two leaf springs 30, 32 as shown are arranged to open in the same direction as the direction of the bristles extending from the bristle plate and are separated by approximately 5 mm along their lower edges. The torsional spring rate of the two leaf springs is between 0.5 and 2.0 Nm/radius. The resonant frequency of the torsion mode of the drive train is a function of the mass moment of inertia and the spring rate.

Extending from spring hub member 26, through spring mount member 28 and forward of the spring mount member approximately 75 mm, is a brush shaft 38. Brush shaft 38 is fixed to both the spring hub member and the spring mount member and is positioned a distance from the axis of rotation of output shaft 16. This distance, referred to as moment arm 43, in the embodiment shown is approximately 6 mm, but could range from 1 to 15 mm. The larger the moment arm, the more torque that is created from the spinning eccentric mass. A conventional brushhead assembly 42 with a set of bristles 44 on a distal end thereof is removably mounted on the brush shaft 38.

An important feature of the V spring member 41 is that it is significantly stiffer in bending motion than in torsional motion. The greater stiffness in bending drives the resonant frequency associated with bending above the desired operating frequency by at least 50 Hz. The torsional mode (resulting in oscillating action of the brushhead assembly) will thus be excited while the bending mode (side-to-side or up/down motion) will not be excited during operation of the toothbrush. This prevents swinging of the spring hub member 26 and the motor 12 during operation, while permitting oscillation of the motor, and resulting oscillation of the brushhead assembly and bristles in a desired manner for cleansing of the teeth, with the frequency and amplitude set out above. In addition to using the V-spring to drive the bending mode frequencies above the desired torsional mode frequencies, support bushings and/or bearings can be used to add stiffness in a desired direction.

Electrical leads 50 and 52 from the battery 15 are connected to leaf springs 30 and 32 at the point where they are mounted in the spring mount member 28. At this point, since the spring mount member is fixed, the distal ends of the leaf springs are also fixed. The leaf springs connect to the positive and negative terminals on the DC motor, completing the electrical circuit. The leaf springs are designed to withstand fatigue and thus can survive the frequency and amplitude of normal operation. By attaching the leads to the fixed end of the leaf springs and completing the electrical connection to the motor through the leaf springs, any difficulty with wires or flying leads breaking due to movement of the leaf springs during normal operation at the frequency and amplitudes indicated above is eliminated.

Figure 3:
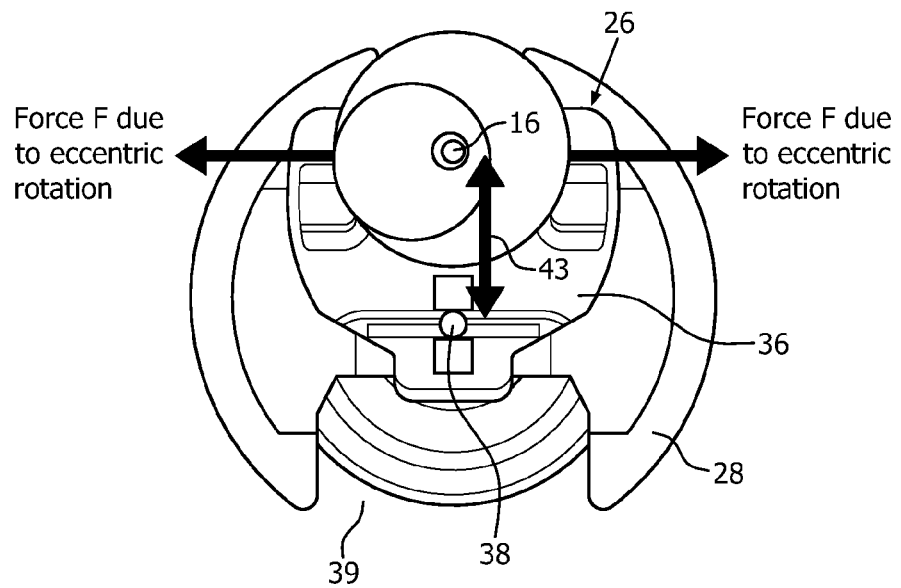
FIG. 3 is a side elevational view of the structure of the toothbrush of FIG. 1.
Figure 4:
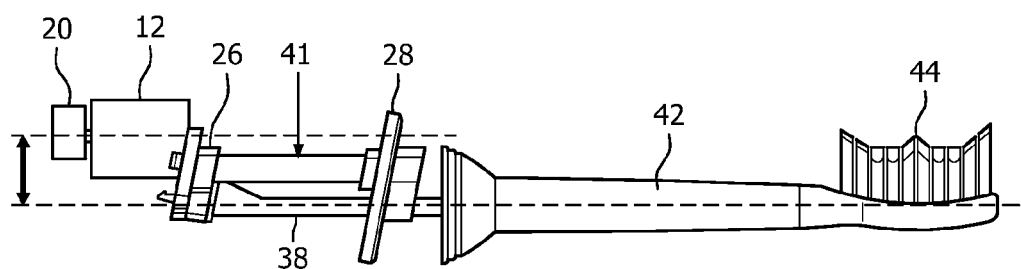
FIG. 4 is a rear elevational view of the toothbrush of FIG. 3.

FIG. 3 shows an end view from the proximal end of the toothbrush opposite from the bristles on the brushhead. It shows in particular the motor axis shaft 16, the brush shaft 38 and the direction of rotation of the motor shaft 16. The moment arm 43, as indicated above, is the distance between the brush shaft 38 and output shaft 14 of the motor. In operation, there is a force created by the rotation of eccentric 20. Since the spring hub member is not restrained, motor 12 oscillates with spring 41 and is hence part of the inertia of the moving, i.e. rotational, system, which comprises the V-spring, the spring hub member, the motor and the eccentric. At the correct frequency, close to the resonant frequency of the rotational system, the force produced by the rotating eccentric excites the V-spring 41 in a resonant torsion mode, which produces the desired oscillating action of the brushhead. In the embodiment shown, the frequency and amplitude are within the range set forth above, but preferably approximately 260 Hz and 10°, respectively.

In operation, V-spring member 41 accomplishes three purposes in the present arrangement. It helps to constrain, i.e. restrict, the motion of the brush shaft 38 to the desired oscillating motion, because the two leaf springs are softer in torsion than in bending; it assists in establishing the resonant frequency of the dynamic (rotational) system; and it provides reliable electrical connections from the battery to the motor.

Accordingly, a mechanical drive train for a power toothbrush has been disclosed which uses a DC motor and an eccentric to excite a spring assembly at or near the resonant frequency of the system. An effective motion of the bristles is produced with a relatively simple and inexpensive driving system involving relatively few individual parts.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. A power toothbrush, comprising
a driving assembly including a battery and a DC motor, the DC motor having a rotating drive shaft extending from one end thereof;
an eccentric member mounted on or connected by another element to the drive shaft and rotatable therewith;
a spring assembly which includes a spring member characterized by a stiffness in torsion which results in a rotational system resonant frequency that is lower than the rotational system resonant frequency from bending stiffness, wherein the motor is mounted to a proximal end of the spring assembly, which is free to move, wherein the other end of the spring assembly is fixed in position;
a brushhead shaft which is mounted to the spring assembly and extends distally therefrom; and
a brushhead, with bristles, attached to the brushhead shaft, wherein in operation the rotation of the eccentric at a selected frequency excites the spring member to an oscillatory action, resulting in the brush shaft, the DC motor, and the brushhead oscillating therewith.

2. The power toothbrush of claim 1, wherein the oscillatory action of the spring member and the brush shaft has a frequency at or near the resonant frequency of the rotational system.

3. The power toothbrush of claim 1, wherein the spring assembly includes at a proximal end a spring hub member and at a distal end a spring mount member, the spring member having the form of a V-spring which is mounted to and extends between the spring hub member and the spring mount member, respectively.

4. The power toothbrush of claim 1, wherein the toothbrush has a rotating inertia and the DC motor is fixed to a rear surface of the spring hub member and moves therewith and the V-spring, such that the motor is part of the rotating inertia of the toothbrush.

5. The power toothbrush of claim 1, wherein the bristles oscillate at a frequency in the range of 100-300 Hz and through an amplitude in the range of 6-14 degree.

6. The power toothbrush of claim 1, wherein the spring member comprises a pair of leaf springs, wherein both leaf springs have a stiffness in torsion which provides a resonant frequency of the rotating system which is lower than the resonant frequency produced by the stiffness of the leaf springs in bending.

7. The power toothbrush of claim 6, wherein the stiffness of the leaf springs in bending results in a resonant frequency of the rotating system which is at least 50 Hz higher than a desired torsional mode resonant frequency, so as to prevent the bending mode from being excited during normal operation of the toothbrush.

8. The power toothbrush of claim 1, wherein the eccentric is a disc having a mass in the range of 0.5-5 grams with an eccentricity of 0.2-5 mm.

9. The power toothbrush of claim 1, wherein the brushhead shaft is offset laterally from the motor drive shaft by a distance in the range of 1-15 mm.

10. A power toothbrush, comprising:
- a driving assembly including a battery and a DC motor, the DC motor having a rotating drive shaft extending from one end thereof;
- an eccentric member mounted on or connected by another element to the drive shaft and rotatable therewith;
- a spring assembly which includes a spring member characterized by a stiffness in torsion which results in a rotational system resonant frequency that is lower than the rotational system resonant frequency from bending stiffness, wherein the motor is mounted to a proximal end of the spring assembly, which is free to move, wherein the other end of the spring assembly is fixed in position;
- a brushhead shaft which is mounted to the spring assembly and extends distally therefrom; and
- a brushhead, with bristles, attached to the brushhead shaft, wherein in operation the rotation of the eccentric at a selected frequency excites the spring member to an oscillatory action, resulting in the brush shaft, the DC motor, and the brushhead oscillating therewith,
- wherein the driving assembly includes electrical leads which connect the battery to the spring member where it is mounted to the spring mount member, such that in operation of the toothbrush, and movement of the spring member, the electrical leads do not move with the movement of the motor.

* * * * *